United States Patent
Boccato et al.

(10) Patent No.: US 9,642,959 B2
(45) Date of Patent: May 9, 2017

(54) ZERO EMISSION DIALYSIS CLINIC

(75) Inventors: Carlo Boccato, Milan (IT); Henning Discher, Berlin (DE); Juergen Kastl, Hong Kong (HK); María Merello De Miguel, Frankfurt (DE); Michael Wild, Bad Homburg (DE)

(73) Assignees: Fresenius Medical Care Italia S.P.A., Cremona (IT); Fresenius Medical Care Deutschland GmbH, Bad Homburg (DE); Deutsche Energie-Agentur GmbH, Berlin (DE)

( * ) Notice: Subject to any disclaimer, the term of this patent is extended or adjusted under 35 U.S.C. 154(b) by 715 days.

(21) Appl. No.: 14/128,389

(22) PCT Filed: Jun. 21, 2012

(86) PCT No.: PCT/EP2012/002627
§ 371 (c)(1),
(2), (4) Date: May 5, 2014

(87) PCT Pub. No.: WO2012/175210
PCT Pub. Date: Dec. 27, 2012

(65) Prior Publication Data
US 2014/0284275 A1   Sep. 25, 2014

Related U.S. Application Data

(60) Provisional application No. 61/499,946, filed on Jun. 22, 2011.

(51) Int. Cl.
*E04H 3/08*   (2006.01)
*F25B 30/06*   (2006.01)
(Continued)

(52) U.S. Cl.
CPC .............. *A61M 1/14* (2013.01); *A61M 1/166* (2014.02); *B01D 61/30* (2013.01); *E04H 3/08* (2013.01);
(Continued)

(58) Field of Classification Search
CPC .......... A61M 1/14; A61M 1/16; A61M 1/166; A61M 1/1662; A61M 1/1664;
(Continued)

(56) References Cited

U.S. PATENT DOCUMENTS 3,352,779 A * 11/1967 Austin ................ A61M 1/1656
137/5
4,678,025 A *  7/1987 Oberlander ............. F24F 1/022
165/48.1

(Continued)

FOREIGN PATENT DOCUMENTS

CN      201 129 040 Y    10/2008
DE   10 2004 034614 A1    2/2006
(Continued)

OTHER PUBLICATIONS

Publication by Simon Perry et al, "Integrated waste and renewable energy to reduce the carbon footprint of locally integrated energy sectors", Energy, published 2008, vol. 33, pp. 1489-1497, made available through Science Direct.*

(Continued)

*Primary Examiner* — Joseph Drodge
(74) *Attorney, Agent, or Firm* — Fish & Richardson P.C.

(57) ABSTRACT

The present invention provides a zero-emission dialysis clinic including a building envelope, daylight concept, lighting concept, mechanical ventilation (71), a chilled and heated ceiling (61) with capillary tubes (60), heat pump (50), and a photovoltaic system (80). Specifically, the present invention balances the energy consumption with energy (Continued)

generation by a photovoltaic system. The $CO_2$ emissions are thus balanced and the building produces no net emissions.

18 Claims, 13 Drawing Sheets

(51) Int. Cl.
  *F24J 2/00* (2014.01)
  *A61M 1/16* (2006.01)
  *B01D 61/30* (2006.01)
  *A61M 1/14* (2006.01)

(52) U.S. Cl.
  CPC ............. *F24J 2/0007* (2013.01); *F25B 30/06* (2013.01); *A61M 2205/36* (2013.01); *F24F 2203/02* (2013.01)

(58) Field of Classification Search
  CPC ...... A61M 2205/36; A61M 2205/3606; A61M 2205/3626; A61M 2205/3646; A61M 2205/366; A61M 2205/362; B01D 61/24; B01D 61/30; E04H 3/08; F24J 2/00; F24J 2/0007; F24J 2/0015; F24J 2/40; F25B 27/00; F25B 27/002; F25B 29/00; F25B 30/00; F25B 30/06; F25B 2300/00; F25B 2500/00; F25B 27/02
  USPC ....... 210/175, 184, 186, 321.6, 321.66, 646, 210/775; 604/4.01, 5.01, 6.09, 6.13; 136/243, 244, 247, 291; 359/592.1, 601; 165/47.1, 48.1, 48.2, 49, 53, 58, 59, 61, 165/901, 902; 62/160, 324.1, 324.6; 52/200, 302.1; 454/196, 199, 205, 250, 454/256
  See application file for complete search history.

(56) References Cited

U.S. PATENT DOCUMENTS

| | | | | |
|---|---|---|---|---|
| 4,970,834 A | | 11/1990 | Polson | |
| 5,247,434 A | * | 9/1993 | Peterson | A61M 1/16 210/646 |
| 5,343,121 A | * | 8/1994 | Terman | H05B 37/02 315/158 |
| 5,863,421 A | * | 1/1999 | Peter, Jr. | A61L 2/04 210/108 |
| 6,041,613 A | * | 3/2000 | Morse | F25B 13/00 62/238.7 |
| 6,251,279 B1 | * | 6/2001 | Peterson | A61L 2/04 134/22.11 |
| 6,385,983 B1 | * | 5/2002 | Sakki | F24F 1/027 62/238.7 |
| 7,975,491 B2 | * | 7/2011 | Smisson, III | A61M 5/36 165/185 |
| 9,265,873 B2 | * | 2/2016 | Ritter | A61M 1/1656 |
| 2003/0177703 A1 | * | 9/2003 | Forbis, Sr. | E04D 13/00 52/3 |
| 2008/0086981 A1 | * | 4/2008 | Kilkis | F24F 5/0089 52/791.1 |
| 2009/0020233 A1 | * | 1/2009 | Berman | E06B 9/32 160/5 |
| 2011/0296769 A1 | * | 12/2011 | Collins | E04B 1/003 52/79.1 |
| 2012/0175296 A1 | * | 7/2012 | Wehmeyer | A61M 1/1654 210/321.69 |

FOREIGN PATENT DOCUMENTS

| | | |
|---|---|---|
| JP | 2009 168256 A | 7/2009 |
| WO | 92/19919 A1 | 11/1992 |
| WO | 96/25214 A1 | 8/1996 |
| WO | 01/41895 A1 | 6/2001 |

OTHER PUBLICATIONS

Publication by Giacomo Bizzarri et al, "New technologies for an effective energy retrofit of hospitals", Applied Thermal Engineering, published 2006, vol. 26, pp. 161-169, made available through Science Direct.*
International Search Report and Written Opinion dated Aug. 26, 2013 in PCT/EP2012/002627.
Kastl et al., "Water Saving in Dialysis Care through the Consequent Use of an Environmental Management System", Blood Purification: Letter to the Editor, 2011, vol. 32:143.

* cited by examiner

ZERO EMISSION DIALYSIS CLINIC

FIELD OF INVENTION

The present invention relates to a zero-emission dialysis clinic to improve the performance of carbon dioxide ($CO_2$) neutral dialysis care.

BRIEF DESCRIPTION

The present invention provides a zero-emission dialysis clinic including a building envelope, a daylight concept, a lighting concept, mechanical ventilation, a heating/cooling system, a heat pump, and a photovoltaic system. Specifically, the present invention balances the energy consumption with energy generation by a photovoltaic system. The $CO_2$ emissions are thus balanced and the building of the present invention produces no emissions.

DETAILED DESCRIPTION

In the present invention, $CO_2$ emissions caused by energy consumption of the building and dialysis treatment are equal to the substituted $CO_2$ emissions of the photovoltaic system. The key components of the zero-emission dialysis clinic of the present invention are: a building envelope, a daylight concept, a lighting concept, mechanical ventilation, a chilled and/or heated ceiling with capillary tubes, a heat pump, and a photovoltaic system.

The building envelope includes all components which separate the heated rooms from the exterior air, soil, and other unheated rooms. Such components include windows, walls, the roof and the floor. A well insulated building envelope with reduced heat bridges and excellent air-tightness can save up to 40% of heating and cooling energy compared to a conventional new building.

Daylight reduces the energy demand for lighting and the cooling load for the HVAC (heating, ventilation, and air-conditioning) systems. The daylight concept of the present invention includes skylights and shading systems with daylight control.

The electric power demand for lighting is minimized by an efficient lighting concept. The lighting concept of the present invention is based on presence-dependent and daylight dependent lighting control and efficient lights.

In the present invention, the air change rate of 1.5/h is supplied by a centralized ventilation system with a heat recovery rate of 85% to reduce ventilation heat losses. Thus, 1.5 times the volume of the room is changed every hour.

In the present invention, heating and cooling energy is supplied to the room by suspended ceilings with integrated capillary tubes. This surface heating and cooling system saves energy by low supply water temperatures and represents a perfect partner for the heat pump. In one embodiment, the heating uses 60 W/m² and cooling uses 80 W/m². The suspended ceilings also provide a positive acoustic effect.

In the present invention, a reversible heat pump (15 $kW_{th}$) provides heating and cooling energy. The heat pump uses warm water from the dialysis units as a heating and cooling source and supplies radiant ceilings for good thermal comfort (see capillary tubes).

In the present invention, the photovoltaic system (112 $kW_p$) on the building roof substitutes the same amount of $CO_2$ that is emitted by the building during operation.

A zero-emission dialysis clinic comprises at least one of the following: a building envelope, a daylight concept, a lighting concept, mechanical ventilation, a heating/cooling system, a heat pump, and a photovoltaic system. The building envelope comprises walls, windows, a roof, and a floor, each of which are all well-insulated. The heating/cooling system comprises a chilled and/or heated ceiling with capillary tubes. The daylight concept comprises skylights and shading systems, said shading systems can have a separate control for a top section and a bottom section. The lighting concept comprises a sensor that senses natural light and/or a sensor that senses the presence of a person nearby, and/or fluorescent lights. The ventilation system comprises an open window near the ceiling and/or adiabatic cooling. The heat pump comprises a reversible heat pump that is supplied with waste water from one or more dialysis systems. The photovoltaic system comprises solar panels on the roof or other exterior surface of the clinic, said solar panels may be mounted on the roof at an angle of 10 degrees.

A further embodiment of the invention comprises a zero emission dialysis clinic comprising: a heating/cooling system and a heat pump. The heating/cooling system comprises a suspended ceiling having a plurality of capillary tubes for receiving fluid therein. The heat pump is connected to at least one dialysis system. The heat pump comprises a reversible heat pump provided with a supply of warm waste water from the dialysis system.

Figure 1:
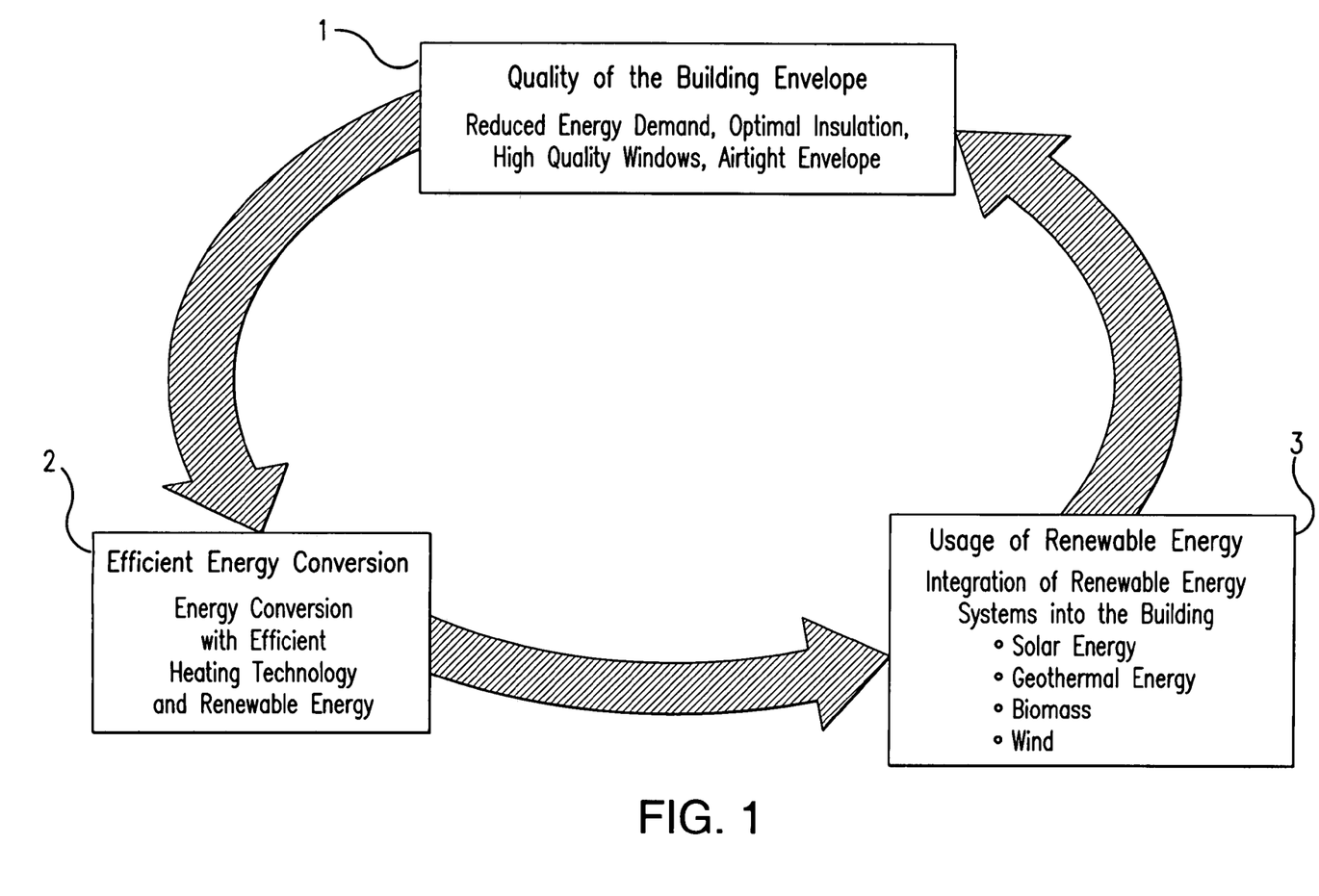
FIG. 1 shows a zero-emissions dialysis clinic building of the present invention.

The present invention further comprises a method for implementing a net zero-emission building. The method comprises: identifying the main energy consumers of the building; reducing the energy demand of the building by a holistic and innovative energy concept; supplying the remaining heating and cooling demand by energy efficient technologies, such as heat pumps; and using renewable energy sources to generate the same amount of $CO_2$ equivalents that are emitted through the energy consumption of the building. The energy demand of the building comprises: the heating demand, the cooling demand, and the electrical energy demand. The heating and cooling demand is reduced by good thermal insulation, a small SA/V (surface area/volume) ratio (compact architecture), optimized window area, and the orientation of the building. The electric energy demand is reduced by efficient lighting and use of natural light. As shown in FIG. 1, three major considerations in such a method for implementing a net zero-emission building include the quality of the building envelope 1 (e.g., reduced energy demand, optimal insulation, high quality windows, airtight envelope), efficient energy conversion 2 (i.e., energy conversion with efficient heating technology and renewable energy), and the usage of renewable energy 3 (i.e., integration of renewable energy systems into the building, e.g., solar energy, geothermal energy, biomass, wind).

Figure 2:
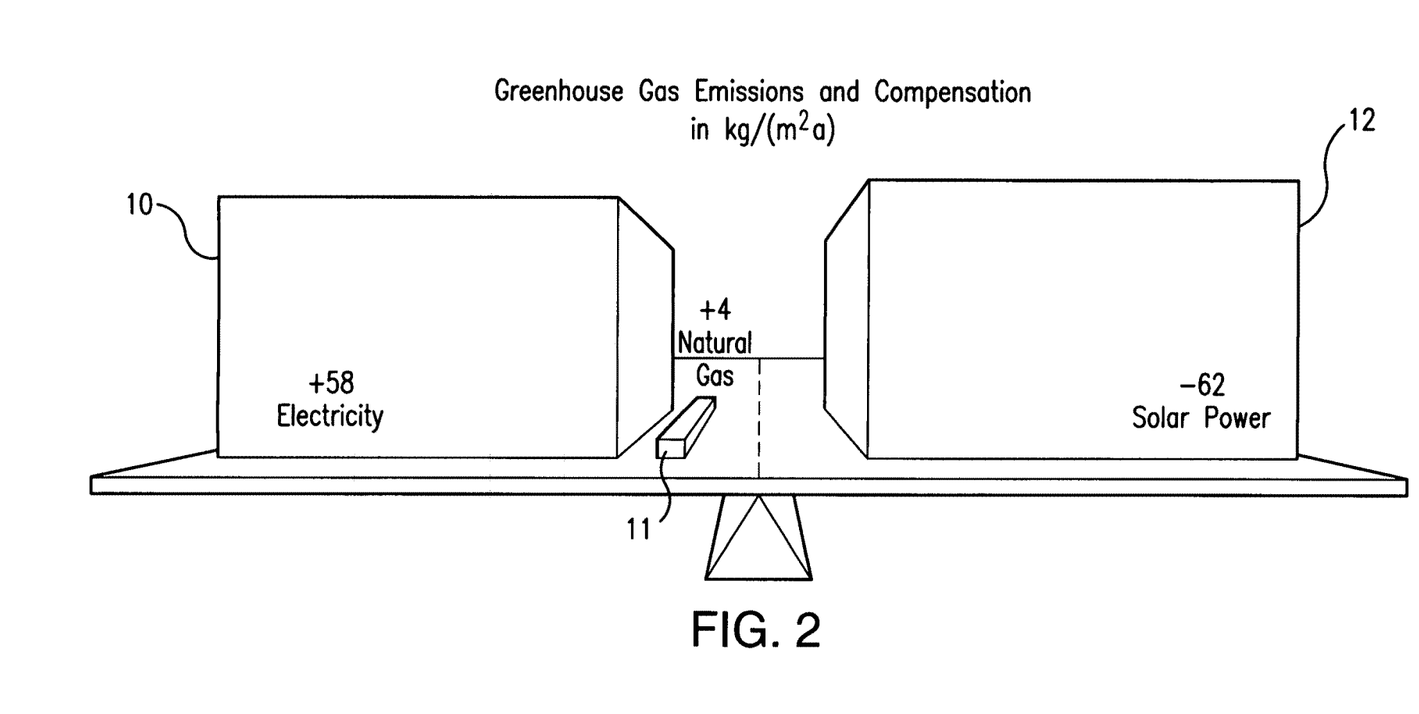
FIG. 2 shows a graphical illustration of the greenhouse gas balance of the present invention.

As shown in FIG. 2, to obtain net zero-emissions, if the greenhouse gas emission generated by the electricity 10 is 58 kg/m$^2$ per year, and the greenhouse gas emission generated by natural gas 11 is 4 kg/m$^2$ per year, then the solar power 12 must compensate for this emission by not generating 62 kg/m$^2$ per year of greenhouse gases.

One embodiment of the zero-emission dialysis clinic of the present invention is designed according to the following specifications. The energy demand of the building is minimized by an excellently insulated building envelope, an optimized orientation, an energy efficient lighting concept, and a centralized mechanical ventilation system with heat recovery. A reversible heat pump as the main heating and cooling energy source achieves high efficiency through the use of warm waste water from the dialysis procedures done inside the building. The building has a final energy consumption of 14.4 MWh per year for gas and 90.0 MWh per year for electricity, which results in the emission of 54.2 tons of $CO_2$ equivalents per year. The photovoltaic system substitutes the same amount and produces 85.6 MWh electric power per year.

The building envelope has an important influence on the energy demand of a building. It includes the outer components such as the floor, roof, exterior walls, doors, and windows. A good thermal insulation reduces heat losses in wintertime (or cold days) and heat gains in summertime (or hot days). Furthermore, thermal bridges are minimized by a detailed design of the building envelope, which includes airtight materials and design to minimize the heat losses through infiltration.

Figure 3A:
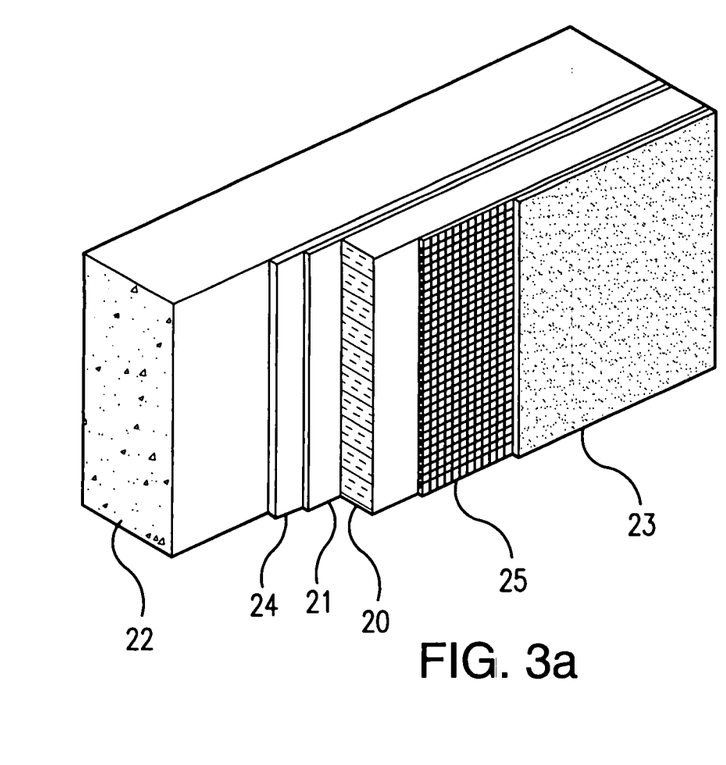
FIG. 3a shows an exemplary embodiment of a wall having insulation of the present invention.

The walls can be insulated by a thermal insulation compound system, as shown in FIG. 3a. An insulation layer 20 can be glued 21 or nailed on the "cold" (exterior) side of the wall 22. The insulation layer 20 is covered by outside plaster 23. Thermal insulation compound systems are a practical cost-efficient way to achieve good thermal insulation. Insulation layer 20 can comprise polystyrene, mineral wool, or other similar insulating materials. FIG. 3a additionally shows the wall is covered by an undercoat 24, glue 21, insulation layer 20, plaster wire 25, and outside plaster 23.

Figure 3B:
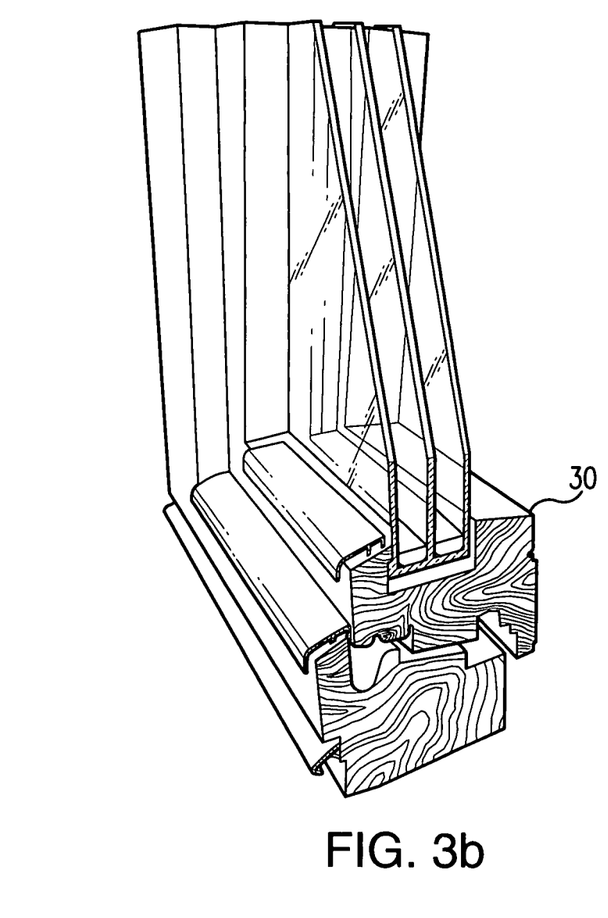
FIG. 3b shows an exemplary embodiment of triple-glazed windows of the present invention.
Figure 4:
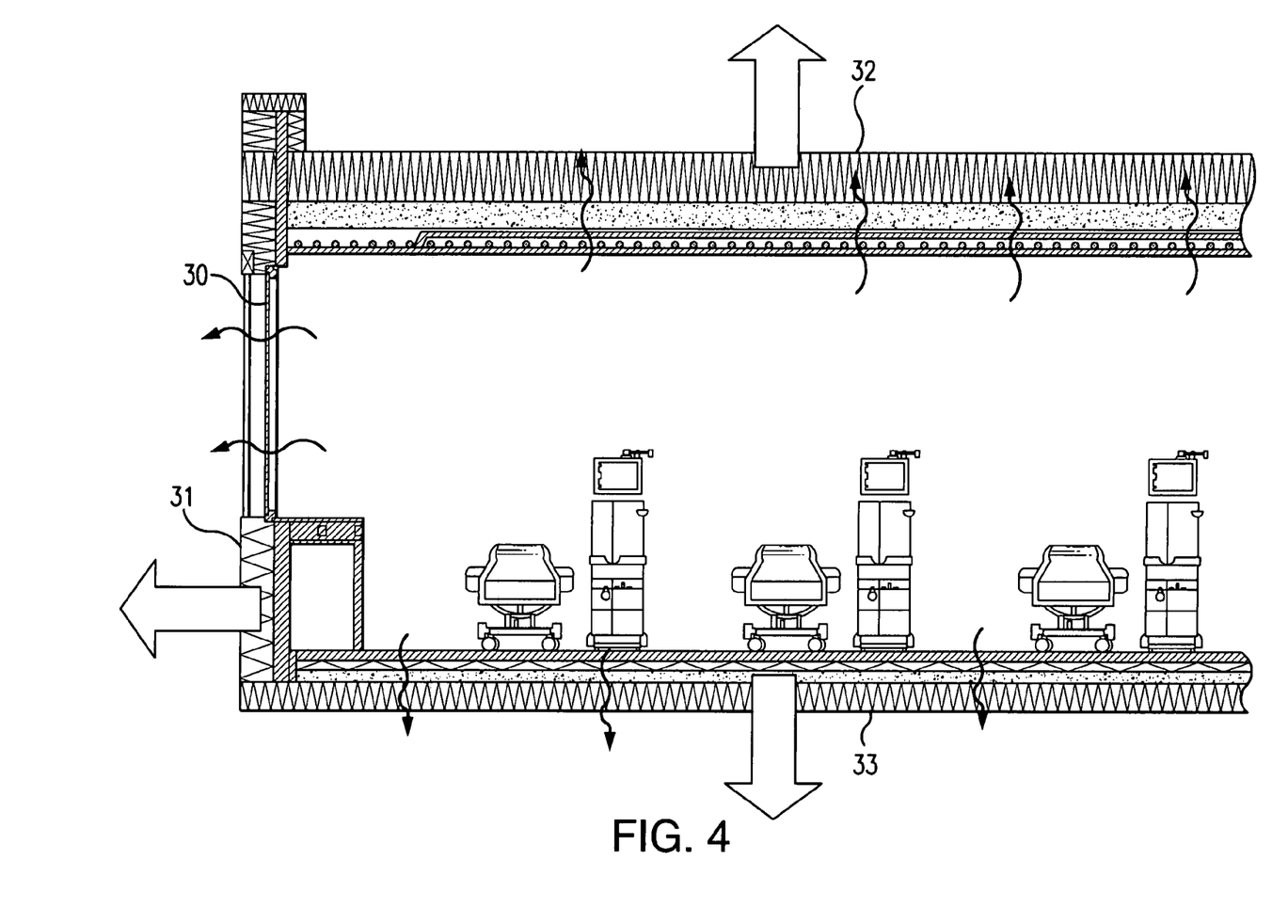
FIG. 4 shows a portion of the building of the present invention illustrating the building envelope.

The energy concept of the zero-emission dialysis clinic of the present invention is based on an increased thermal insulation standard. The g-value (total energy transmittance rate) should be as high as possible to improve solar heat gains in wintertime (or on cold days) and improve light transmission to reduce energy consumption by electric light. In a preferred embodiment of the instant invention, a g-value of 0.5 (50%) is achieved. The U-values (heat transfer coefficients) of certain aspects of the building are well above the German standards. Specifically, this preferred embodiment includes triple glazed windows 30 (see FIG. 3b). As shown in FIG. 4, windows 30 have a Uvalue of 0.8 W/(m$^2$K), outside walls 31 have a U-value of 0.15 W/(m$^2$K), a roof 32 has a U-value of 0.13 W/(m$^2$K), and a floor 33 has a U-value of 0.18 W/(m$^2$K). The airtight construction (n50=0.6/h) and reduced thermal bridges help save about 40% of the heating and cooling energy compared to a conventional building. The windows 30 are approximately 42% better insulated than the German standards, the roof 32 is 37% better insulated than German requirements, and the floor 33 is 51% better insulated than German requirements. The outside walls 31 comply with 43% of the German Energy Saving Ordinance (ENEV 2009 "Verordnung zur Änderung der Energieeinsparverordnung" as issued in 2009 by the Government of the Federal Republic of Germany). The ENEV also specifies a lower level of air tightness ($n_{50max}$=1.5/h) than the present invention.

Figure 5:
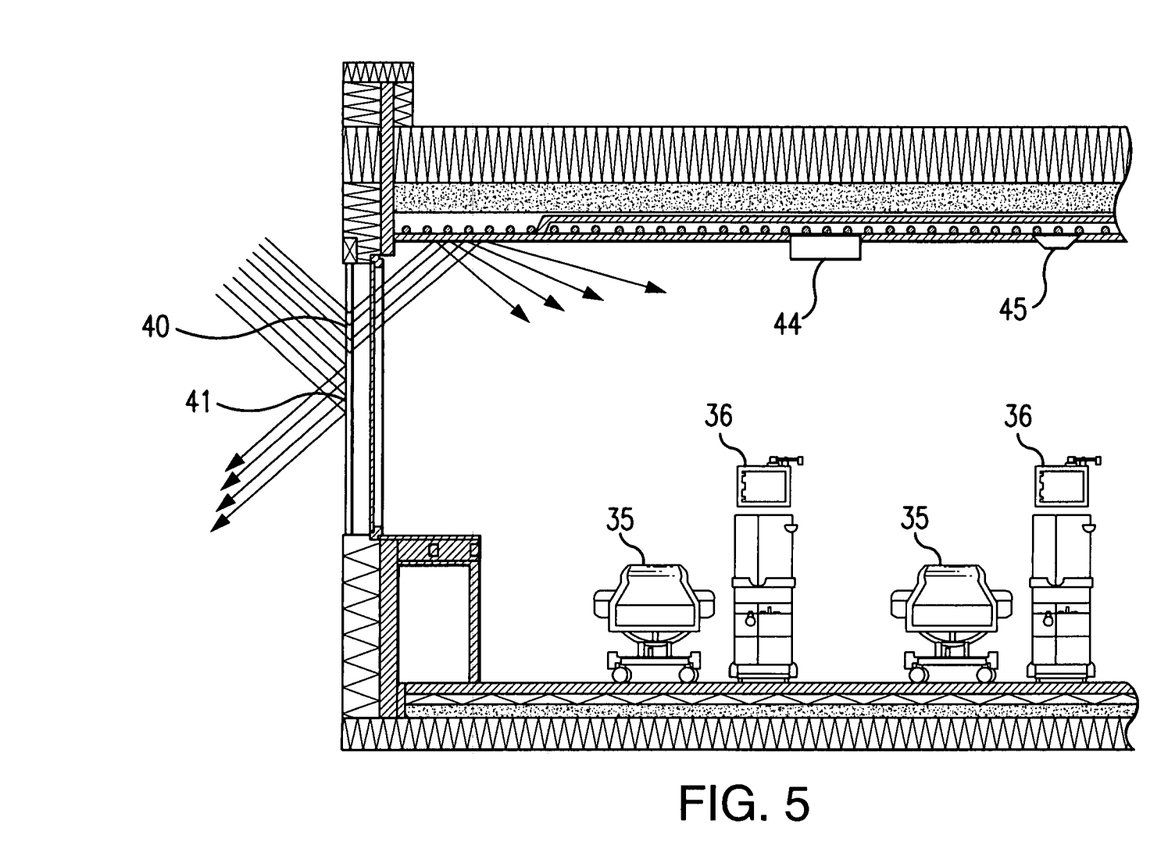
FIG. 5 shows a portion of the building of the present invention illustrating the lighting concept.
Figures 6A, 6B, 6C:
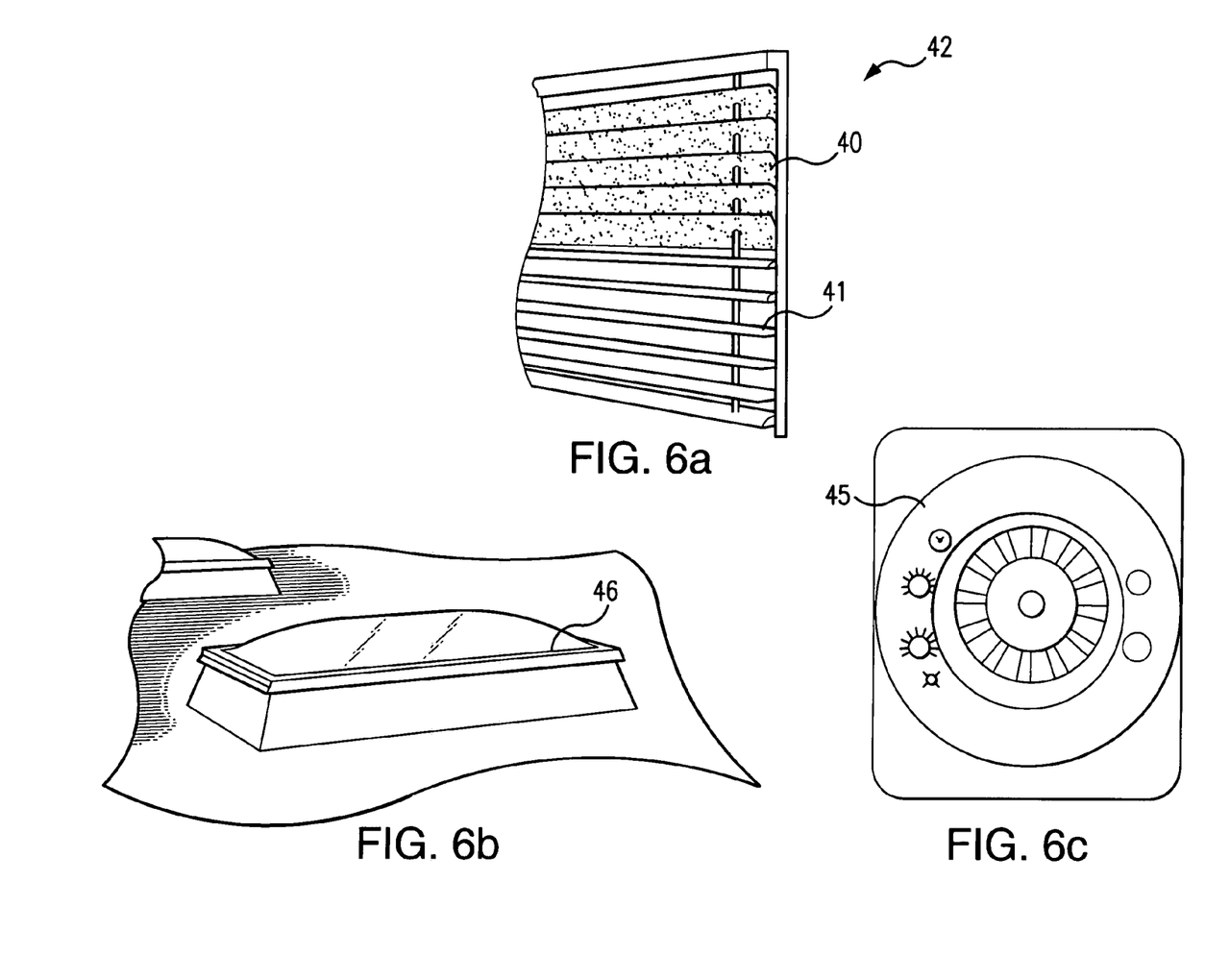
FIG. 6a shows an external sun-shading of the present invention.
FIG. 6b shows a daylight/presence sensor of the present invention.
FIG. 6c shows a skylight of the present invention.

The electric energy demand for lighting accounts for about 11% of the electricity energy demand of the building. The lighting concept of the present invention maximizes daylight use, as seen in FIG. 5, in a building which contains patient beds 35 and dialysis machines 36. As shown in FIG. 5 and FIG. 6a, the upper part 40 and lower part 41 of the external sun-shading 42 can be turned independently. The lower part 41 can thus be closed to reflect the sun and thus to reduce the cooling load in summertime. At the same time, the upper part 40 is used to direct daylight into the room to reduce energy consumption for electric lighting. Surface mounted lights (or luminaries) 44 may be controlled by daylight and presence sensors 45, as shown in FIG. 5 and FIG. 6b. The presence control sensor 45 ensures that light is there when it is needed, i.e., when a person is present in the room. The daylight control sensor 45 automatically adjusts the artificial lighting depending on the available natural daylight. The daylight and presence sensors 45 can be included on the lights or can be located independently therefrom. The daylight and presence sensor 45 can be combined or be independent sensors that wirelessly (or wiredly) communicate with each other.

As shown in FIG. 6c, one advantage of a one-floor building is that skylights 46 in the ceiling can be used for receiving more daylight into the room. For example, over 20 skylights can be placed in areas without windows in the walls to help conserve electricity. Current skylights have good thermal characteristics, with U-values of up to 1.2 W/(m$^2$K) and can also be used for natural ventilation.

An energy efficient control system maximizes the use of daylight and thus minimizes the demand for electric lighting. The electric lights used are preferably fluorescent lights with incorporated starter and ballasts, which save up to 90% energy and have a very long lifetime.

Figure 7A:
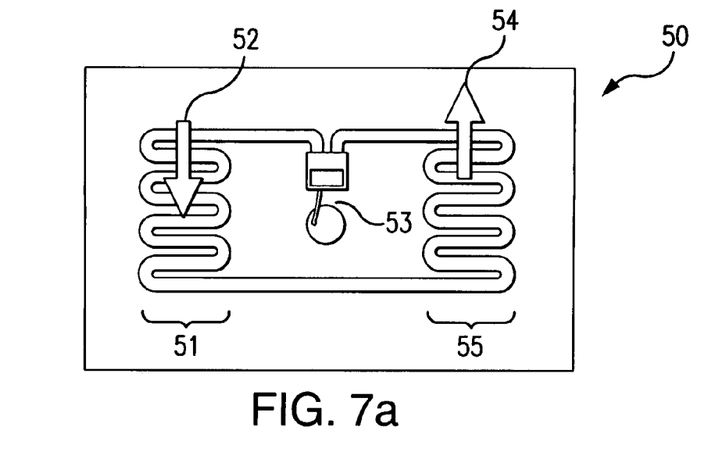
FIG. 7a shows a heat pump of the present invention.

In a preferred embodiment, the reversible heat pump 50 as shown in FIG. 7a is the main source for heating and cooling energy and covers more than 50% of the heating energy demand and more than 70% of the cooling energy demand of the building. In another embodiment, the heat pump 50 covers about 50% of the heating energy demand and about 70% of the cooling energy demand. In another embodiment, the heat pump covers about 40% of the heating energy demand and about 60% of the cooling energy demand. In another embodiment, the heat pump covers about 40% to about 60% of the heating energy demand and about 60% to about 80% of the cooling energy demand.

Figure 7B:
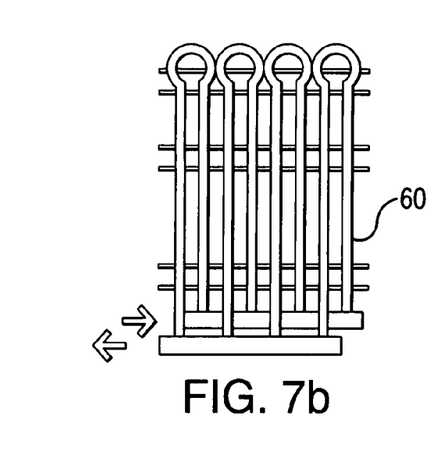
FIG. 7b shows an embodiment of capillary tubes of the present invention.

In accordance with the embodiment depicted in FIG. 7a, the evaporator section 51 of heat pump 50 is supplied by warm waste water 52 from a dialysis machine 36 or another medical device. The dialysis machine 36 is a conventional dialysis machine, as known in the art. Since the dialysis fluid must be heated to about body temperature before use, and remains warm after use, the heat pump 50 takes advantage of this heat energy. The heat pump transfers the heat from the waste fluid to a useable temperature level of about 30-35° C. (86-95° F.), more preferably about 31-34° C., and most preferably about 32-33° C. To run this process, electric energy for the compressor 53 is necessary, and the heating energy 54 is extracted from the condenser portion 55 of the heat pump. The temperature difference between the heat source (waste water 52) and the heating system should be small to achieve a good efficiency of the heat pump 50. The present invention uses a surface heating system, such as capillary tubes 60 as shown in FIG. 7b, which are integrated into a suspended ceiling 61 (See FIG. 8). A gas condensing boiler 62 (See FIG. 12 and FIG. 13) is activated as a back-up in case the heating demand of the building exceeds the power of the heat pump 50.

Figure 8:
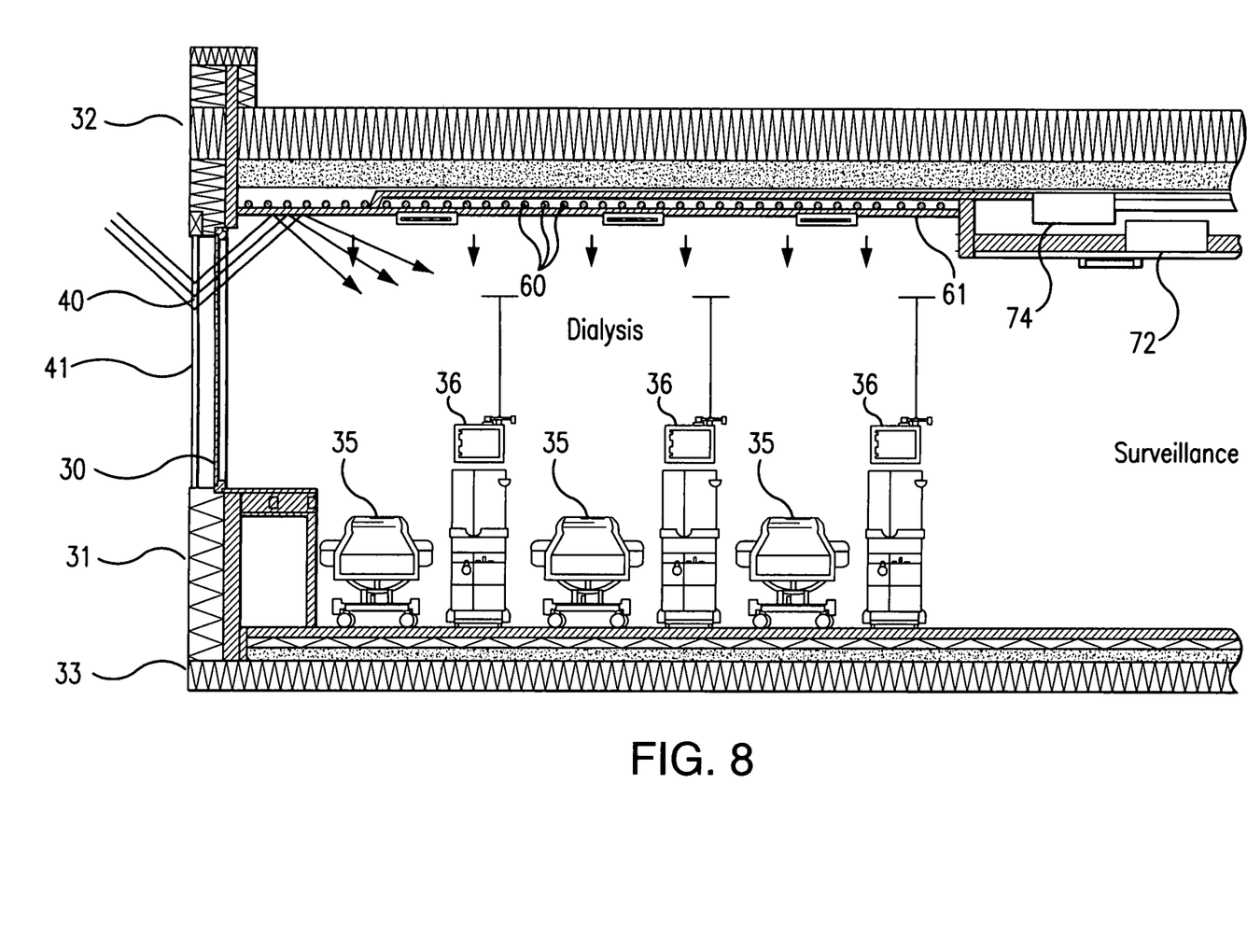
FIG. 8 shows a portion of the building of the present invention illustrating the heating/cooling energy.

The heat pump 50 is reversible and thus can also cool the building in the summertime (or on warm days). As shown in FIG. 8, using the capillary tubes 60 in the suspended ceiling 61, a surface temperature of about 18° C. (64.4° F.) can be reached in the rooms. The cold water is supplied by the heat pump 50 working as a compression chiller in combination with a hybrid cooling tower 91 (See FIG. 12 and FIG. 13), as known in the art.

One embodiment of the suspended ceiling 61 includes integrated capillary tubes 60 that comprise long plastic tubes mounted in loops, as shown in FIG. 7b and FIG. 8. In the summertime (or on warm days), cold water circulates through the tubes 60 and absorbs higher thermal energy from the rooms. In wintertime (or on cold days), warm water is circulated through the tubes 60 and transfers the heat energy via thermal radiation into the rooms. Excellent comfort without any air draft or noise emissions is achieved by the heating/cooling system of the present invention.

The electric energy demand for mechanical ventilation accounts for about 6% of the electricity energy demand of the building. A key element to achieve efficient ventilation is the high air tightness of the building, which avoids infiltration heat loss. However, a supply of fresh air 70 is needed in the building for improved air quality. The ventilation system 71 of the present invention supplies fresh air to the building users and reduces the risk of mold.

Figure 9:
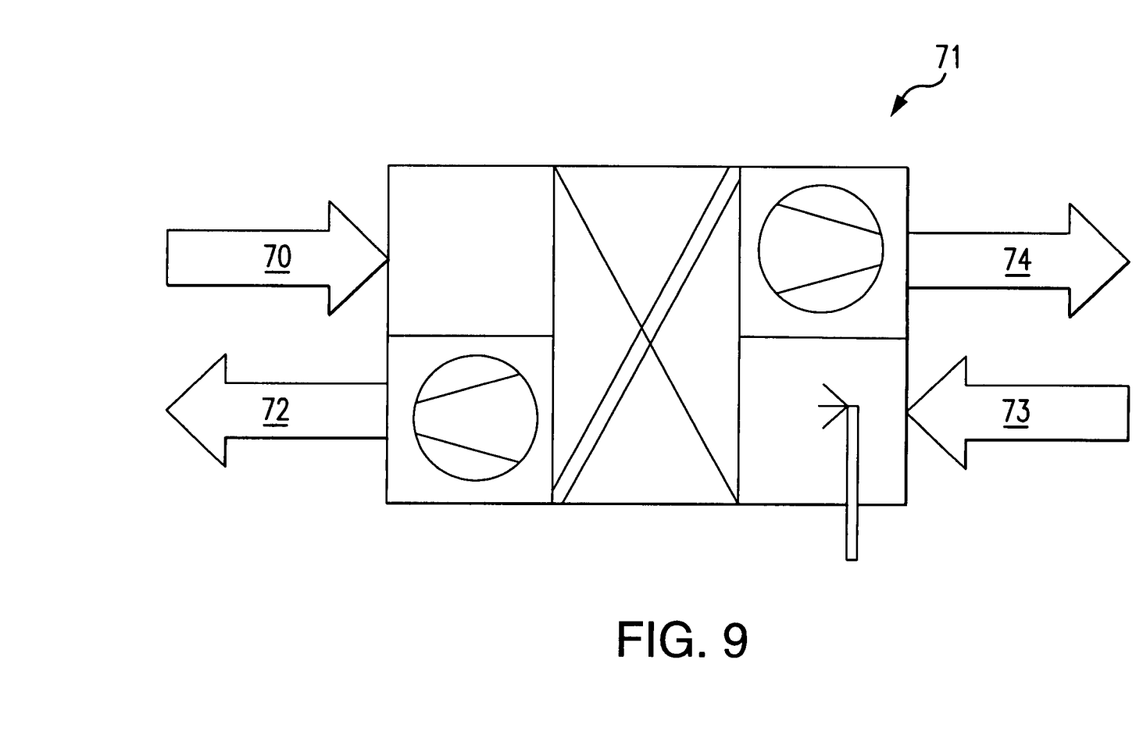
FIG. 9 shows a ventilation system of the present invention.
Figure 10:
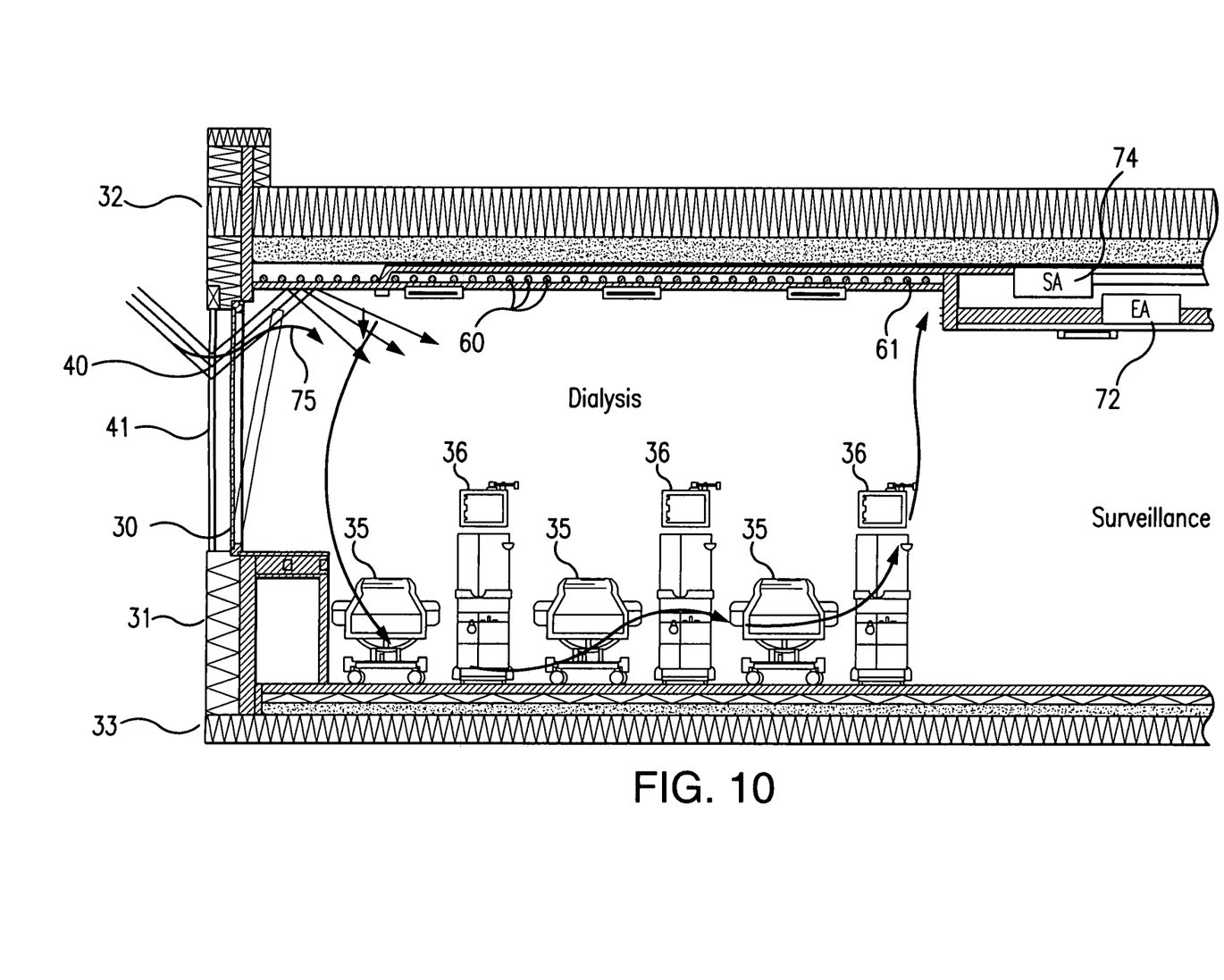
FIG. 10 shows a portion of the building of the present invention illustrating the ventilation system.

As shown in FIG. 9, the centralized mechanical ventilation system 71 with an effective heat recovery of about 85% saves heating energy in the wintertime (or on cold days) by recovering energy from exhaust air 72 and return air 73. The supply air 74 will be cooled through adiabatic cooling in the summer or on warm days. The heat recovery system transfers evaporation cooling energy to chill the supply air. No additional electricity is required to reduce the cooling demand. Alternatively, as depicted in FIG. 10, air can be provided to the building by ventilation 75 through a window 30.

Figure 11A:
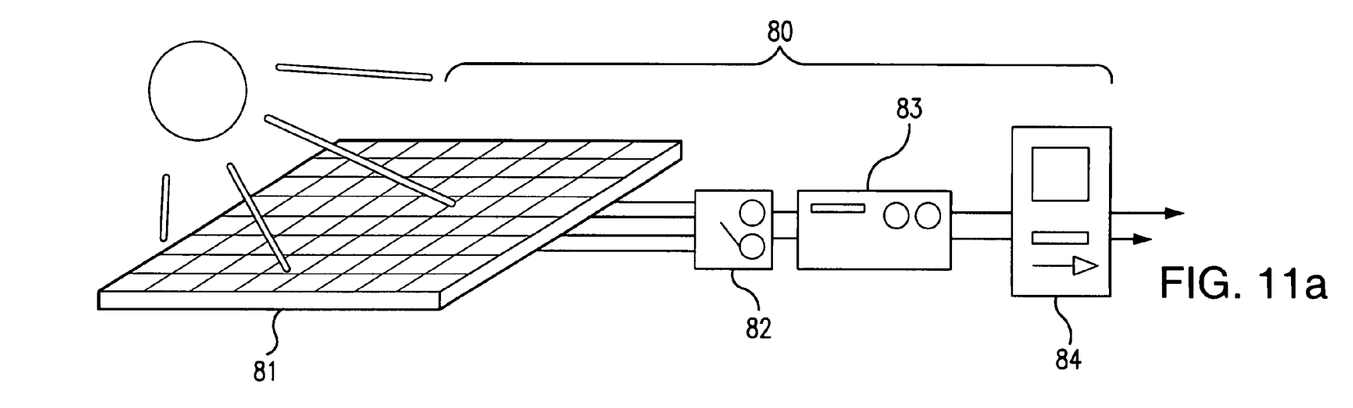
FIGS. 11a and 11b show the photovoltaic system of the present invention.

As shown in FIG. 11a, photovoltaic (PV) systems 80, e.g., including a PV module 81, direct current main switch 82, inverter 83, and electricity meter 84, convert solar radiation into electricity. Such renewable energy technology does not produce $CO_2$ during the energy generation process and can be used to compensate for the $CO_2$ released by the conventional systems. About 633 kg of $CO_2$ equivalents can be saved by 1 MWh of photovoltaic electricity compared to the German electric power mix.

In one embodiment of the present invention, the photovoltaic system 80 on the roof of the clinic building generates about 85-90 MWh per year. This equals the electric energy demands of 22 three-person family households (in Germany) per year. The generated electric energy of 85-90 MWh per year substitutes about 55 tons of $CO_2$ equivalents, which equates to the annual energy demand of the dialysis clinic of the present invention. Thus, the energy production and consumption of the dialysis clinic of the present invention is balanced and there are net zero-emissions.

Figure 11B:
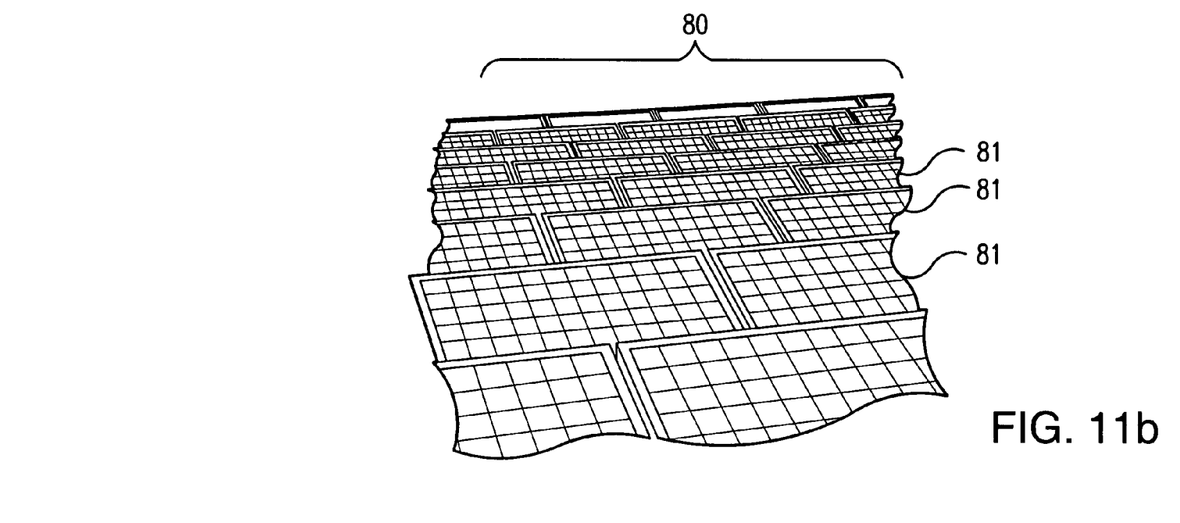

In one embodiment, a portion of which is depicted in FIG. 11b, the photovoltaic system 80 of the present invention includes 460 panels (or modules) 81 with a surface area of about 767 $m^2$ and has a capacity of 112 kWp. In another embodiment, the photovoltaic system could include about 400-460 panels 81. The panels 81 are preferably inclined at an angle of about 10°, which allows draining of rain water and minimizes the soiling of the surface of the panels 81. This low angle reduces the efficiency of each single panel 81 but allows the positioning of more panels 81 on the roof. A higher angle would cause more shading and would therefore limit the possible number of panels 81. In other embodiments, the angle of incline could be between 5° and 15°, between 10° and 20°, or between 8° and 12°.

Figure 12:
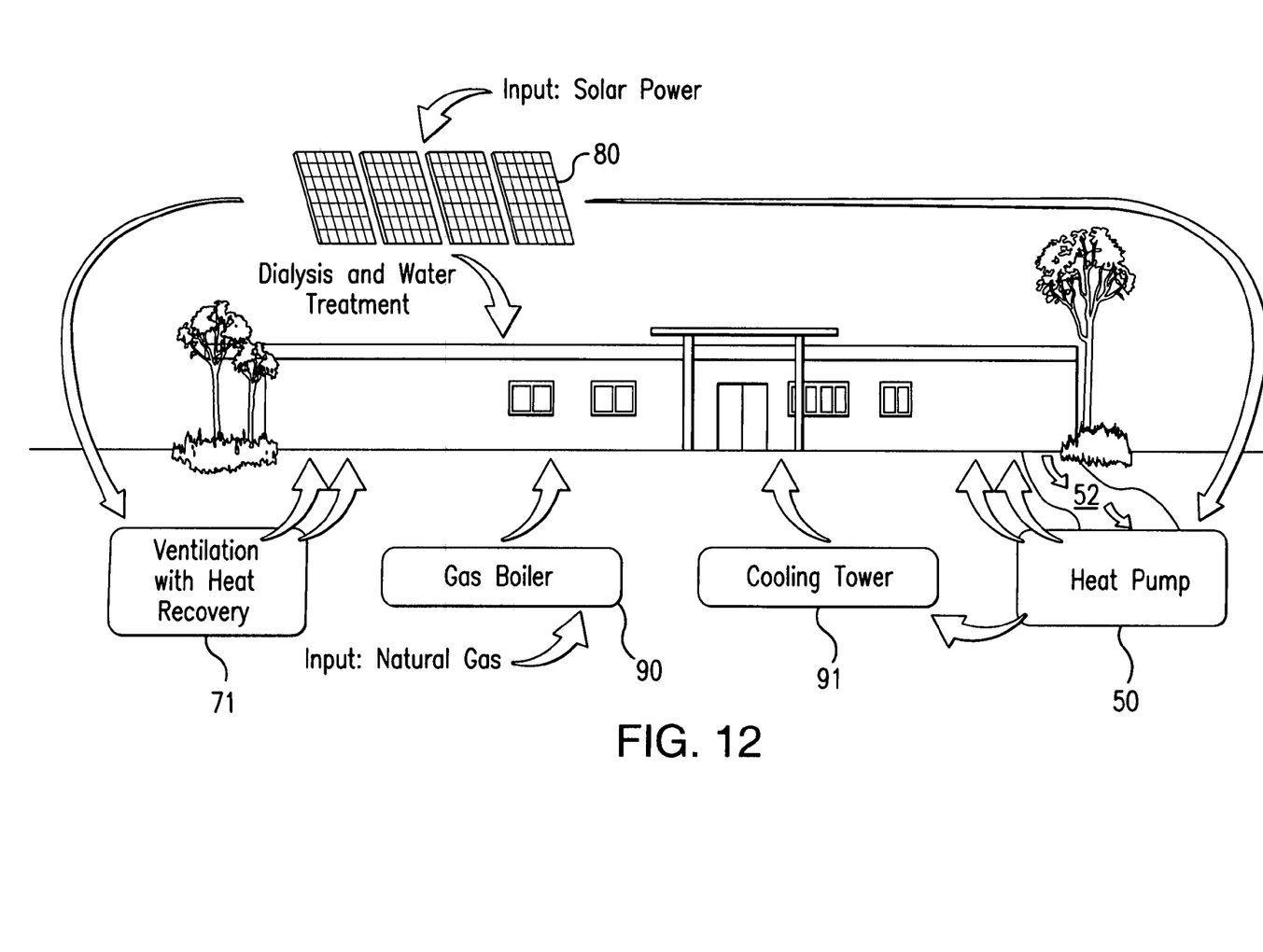
FIG. 12 shows the building of the present invention illustrating the energy flow and consumption.
Figure 13:
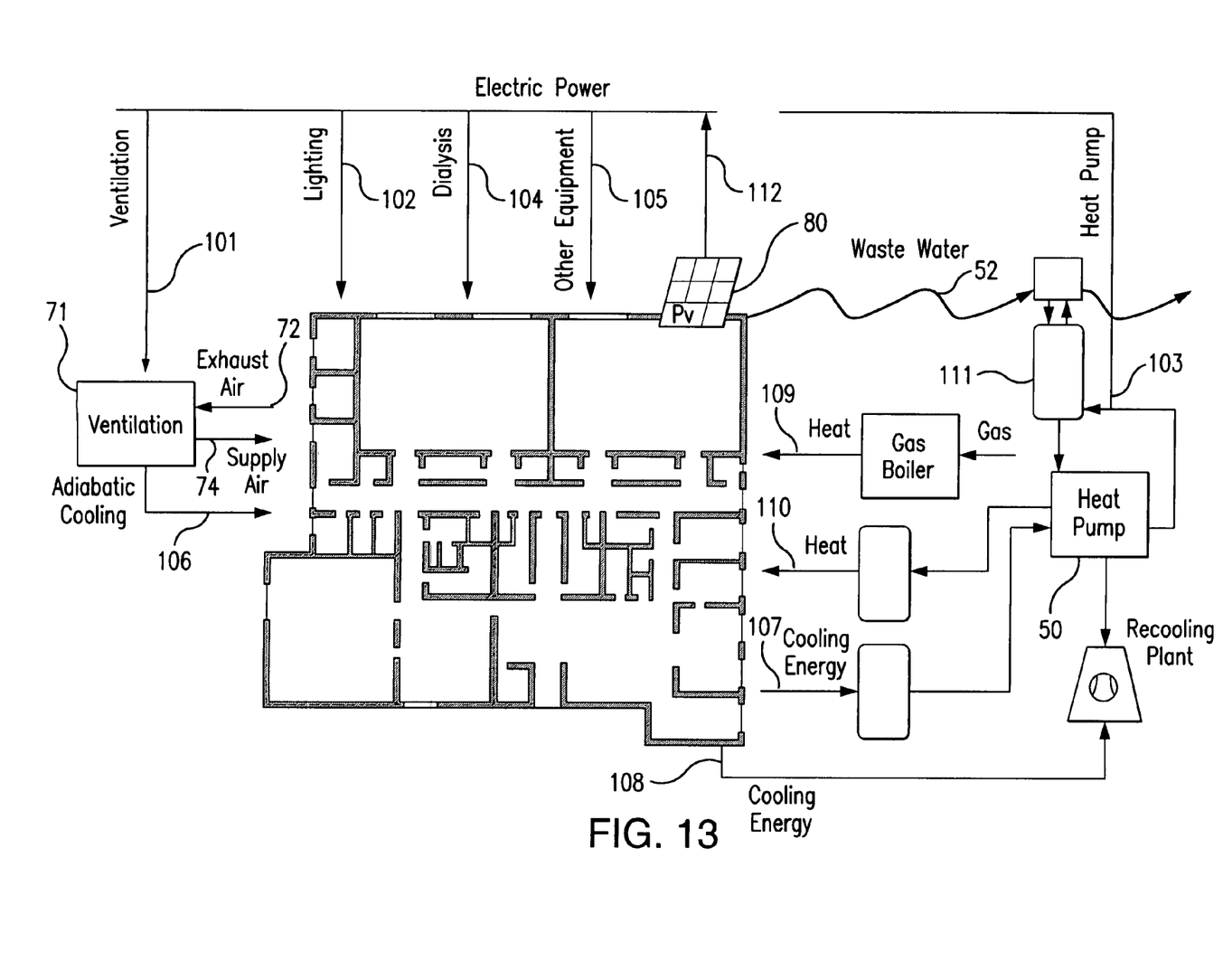
FIG. 13 shows the building of the present invention illustrating the energy flow and consumption.

FIG. 12 and FIG. 13 show the energy flow and consumption of the dialysis clinic building. As shown in FIG. 12, energy inputs to the building include PV system 80 powered by solar power and gas boiler 90 powered by natural gas, so as to power the use of mechanical ventilation system 71, heat pump 50 (which also receives energy from wastewater 52), the operation of a cooling tower 91, and dialysis machines 36. Treatment processes for water may also be powered by the PV system (not depicted). As shown in FIG. 13, the main electric energy consumers in the building are the mechanical ventilation system 101 (Q=5.2 kWh/m2 per year), the lighting system 102 (Q=10.0 kWh/m2 per year), the heat pump 103 (Q=7.1 kWh/m2 per year), the dialysis treatment equipment 104 (Q=59.2 kWh/m2 per year), and other equipment 105 (e.g., PCs, domestic hot water, etc.) (Q=10.0 kWh/m2 per year). The cooling energy demand for ventilation is covered by adiabatic cooling 106 (Q=3.2 kWh/m2 per year). The remaining cooling energy is supplied by a reversible heat pump in cooling mode 107 (Q=8.3 kWh/m2 per year) and free cooling 108 via heat rejection. Heating energy is mainly supplied by the heat pump 110 (Q=18.3 kWh/m2 per year) and a smaller part by a condensing gas boiler 109 (Q=15.0 kWh/m2 per year) which operates as the back-up system. The heat source for the heat pump is warm waste water from the dialysis 111 (Q=13.1 kWh/m2 per year). The photovoltaic system 112 on the rooftop of the building generates sufficient electric energy (Q=98.4 kWh/m2 per year) to compensate for the CO2 emissions of the building's energy consumption.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

The invention claimed is:

1. A dialysis clinic comprising:
a building comprising one or more fluid tubes;
a plurality of dialysis systems located in the building;
a building heating and cooling system comprising a heat pump that is fluidly connected to the one or more fluid tubes and that is fluidly connected to the dialysis systems via fluid conduits such that the heat pump can receive waste liquid from the plurality of medical systems via the fluid conduits for heating or cooling a fluid in the heat pump, the heat pump being configured to circulate the heated or cooled fluid through the one or more fluid tubes for heating or cooling the building;
a window shading system configured to control an amount of daylight allowed to enter the building via an associated window;
a plurality of lighting elements to illuminate the building;
a mechanical ventilation system configured to supply fresh air to the building; and
a photovoltaic system comprising one or more solar panels disposed outside the building and configured to supply electrical energy to the building.

2. The dialysis clinic of claim 1, wherein the building comprises walls, windows, a roof and a floor which are all insulated.

3. The dialysis clinic of claim 1, wherein the one or more fluid tubes are located in a ceiling of the building.

4. The dialysis clinic of claim 1, wherein the dialysis system comprises a plurality of skylights and a plurality of window shading systems.

5. The dialysis clinic of claim 4, wherein each of the plurality of window shading systems comprises a first control for a top section of a window shade of the window shading system and a second control for a bottom section of the window shade of the window shading system.

6. The dialysis clinic of claim 1, wherein the dialysis clinic comprises a sensor configured to sense natural light for controlling the plurality of lighting elements.

7. The dialysis clinic of claim 1, wherein the dialysis clinic comprises a sensor configured to sense the presence of a person in a room of the clinic for controlling the plurality of lighting elements.

8. The dialysis clinic of claim 1, wherein the lighting elements comprise fluorescent lights.

9. The dialysis clinic of claim 1, wherein the mechanical ventilation system comprises an opening in a ceiling of the building.

10. The dialysis clinic of claim 1, wherein the photovoltaic system comprises solar panels on a roof of the clinic.

11. The dialysis clinic of claim 10, wherein the solar panels are mounted on the roof at an angle of about 10 degrees from horizontal.

12. The dialysis clinic of claim 1, wherein the heat pump is a reversible heat pump.

13. A medical clinic comprising:
a building comprising one or more fluid tubes;
a plurality of dialysis systems located in the building; and
a building heating and cooling system comprising a heat pump that is fluidly connected to the one or more fluid tubes and that is fluidly connected to the dialysis systems via fluid conduits such that the heat pump can receive waste liquid from the plurality of medical systems via the fluid conduits for heating or cooling a fluid in the heat pump, the heat pump being configured to circulate the heated or cooled fluid through the one or more fluid tubes for heating or cooling the building.

14. The medical clinic of claim 13, wherein the heat pump is a reversible heat pump.

15. The medical clinic of claim 13, wherein the heat pump is supplied with waste liquid from each of the plurality of dialysis systems.

16. The medical clinic of claim 13, wherein the plurality of dialysis systems are configured to supply the waste liquid to the heat pump.

17. A method comprising:
transferring waste liquid from a plurality of medical dialysis systems located in a building to a heat pump of a building heating and cooling system via fluid conduits that fluidly connect the dialysis systems to the heat pump, the building heating and cooling system comprising one or more fluid tubes in the building, the one or more fluid tubes being fluidly connected to the heat pump, the heat pump using the waste liquid to heat or cool a fluid in the heat pump; and
circulating the heated or cooled fluid through one more fluid tubes in the building to heat or cool the building.

18. The method of claim 17, wherein the heat pump is a reversible heat pump.

* * * * *